United States Patent
Bitter

(10) Patent No.: US 9,869,632 B2
(45) Date of Patent: Jan. 16, 2018

(54) ABSORPTION SPECTROMETER AND METHOD FOR MEASURING THE CONCENTRATION OF A GASEOUS COMPONENT OF INTEREST IN A MEASUREMENT GAS

(71) Applicant: Siemens Aktiengesellschaft, Munich (DE)

(72) Inventor: Ralf Bitter, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 191 days.

(21) Appl. No.: 14/823,248

(22) Filed: Aug. 11, 2015

(65) Prior Publication Data

US 2016/0047739 A1    Feb. 18, 2016

(30) Foreign Application Priority Data

Aug. 13, 2014    (EP) .................................. 14180764

(51) Int. Cl.
*G01N 21/31* (2006.01)
*G01N 33/00* (2006.01)
(Continued)

(52) U.S. Cl.
CPC .............. *G01N 21/31* (2013.01); *G01J 3/433* (2013.01); *G01N 21/3504* (2013.01);
(Continued)

(58) Field of Classification Search
CPC .... G01N 21/31; G01N 21/39; G01N 21/3504; G01N 33/0073; G01N 2201/061; G01J 3/433
See application file for complete search history.

(56) References Cited

U.S. PATENT DOCUMENTS 5,173,749 A * 12/1992 Tell ...................... G01N 21/031
                                                               250/343
5,317,156 A *  5/1994 Cooper .................. G01N 21/39
                                                              250/339.13
(Continued)

FOREIGN PATENT DOCUMENTS

| JP | H05-79976 | 3/1993 |
| JP | 2004-361129 | 12/2004 |
| WO | WO 2012/109030 | 8/2012 |

OTHER PUBLICATIONS

English translation of Kumazawa et al. (JP2004361129 (A))—Dec. 24, 2004.*

*Primary Examiner* — Dominic J Bologna
(74) *Attorney, Agent, or Firm* — Cozen O'Connor

(57) ABSTRACT

Absorption spectrometer and method for measuring the concentration of a gaseous component of interest in a measurement gas, wherein to compensate influence of changes in an optical path length in the absorption spectrometer on a measured result, light from the laser is modulated with at least one pilot frequency in the MHz range, the measurement signal is analyzed in a phase-sensitive manner for the pilot frequency, phase information obtained during this analysis is compared with phase information obtained during calibration of the absorption spectrometer, where the measured result is corrected as a function of the difference between the two items of phase information. Alternatively, light from the laser is modulated with two pilot frequencies, where signal components contained in the measurement signal with the pilot frequencies are detected in a phase-sensitive manner and the difference between the phase information of the two signal components obtained in this operation is analyzed.

16 Claims, 6 Drawing Sheets

(51) Int. Cl.
*G01N 21/3504* (2014.01)
*G01J 3/433* (2006.01)
*G01N 21/39* (2006.01)

(52) U.S. Cl.
CPC ......... *G01N 21/39* (2013.01); *G01N 33/0073* (2013.01); *G01N 2201/061* (2013.01)

(56) References Cited

U.S. PATENT DOCUMENTS

| | | |
|---|---|---|
| 2008/0123712 A1* | 5/2008 | Zhou ................ G01N 21/39 372/55 |
| 2012/0113426 A1 | 5/2012 | Rao |
| 2012/0188549 A1 | 7/2012 | Hoshino et al. |
| 2013/0163000 A1 | 6/2013 | Ido et al. |

* cited by examiner

ABSORPTION SPECTROMETER AND METHOD FOR MEASURING THE CONCENTRATION OF A GASEOUS COMPONENT OF INTEREST IN A MEASUREMENT GAS

BACKGROUND OF THE INVENTION

1. Field of the Invention

The invention relates to an absorption spectrometer for measuring the concentration of a gaseous component of interest in a measurement gas.

2. Description of the Related Art

WO 2012/109030 A1 discloses an absorption spectrometer and method. Laser spectrometers are employed for optical gas analysis, e.g., in process measurement technology. A laser, as a rule a laser diode, generates light in the infrared region in this respect, which is routed through a gas to be measured (process gas) and then detected. The wavelength of the light is tuned to a specific absorption line of the respective gaseous component to be measured, to which end the laser diode is usually activated periodically with a sawtooth or triangular current signal to periodically scan the absorption line with the generated light in a wavelength-dependent manner.

In the case of direct absorption spectroscopy, the concentration of the gaseous component of interest is determined immediately from the reduction in light intensity (absorption) detected at the location of the absorption line. In the case of wavelength-modulation spectroscopy, the wavelength of the generated light is additionally modulated sinusoidally with a comparatively high frequency in the kHz range and with small amplitude, during the comparatively slow wavelength-dependent scanning of the absorption line. The profile of the absorption line is not linear. As a result, higher-order harmonics are generated in the detector signal or measurement signal. The measurement signal is demodulated in the case of a higher-order harmonic of this type, preferably the second harmonic, by a phase-sensitive lock-in technique, and analyzed to produce a measured result for each scanning interval. The analysis is effected, for example, by curve-fitting the demodulated measurement signal profile to be expected in the ideal case and as described analytically by using an approximation model (target curve) to its actual profile (actual curve). Since one of the parameters of the approximation model is proportional to the concentration of the gaseous component, what is obtained from the analysis and therefore the measured result is the concentration of the gaseous component to be measured.

Wavelength-modulation spectroscopy is particularly advantageous for measuring low concentrations because it is better able to filter out noise from the measurement signal. At higher concentrations, however, the approximations necessary for the analysis of the measurement signal become increasingly inaccurate, with the result that measurement error rises. In the case of absorption spectroscopy, on the other hand, measurement error is higher due to the higher noise sensitivity in the case of small concentrations. But since an approximation description of the absorption line is not necessary, measurement accuracy becomes better with increasing concentration as the useful signal then also becomes stronger.

The size of the measurement signal is inversely proportional to the absorption of the light on the path from the laser to the detector. For its part, the absorption at the location of the specific absorption line shows a monotonic dependency in accordance with the Lambert-Beer law, which is approximately proportional during most measurement tasks, to the product of the concentration of the gaseous component of interest and the length of the light path between the laser and the detector. The lower the concentrations to be measured, the longer the absorption distance has to be in order to obtain an adequately large measurement signal. Whereas in the case of in-situ measurements, long absorption distances are present as a rule because of the constructional nature of the process plant (e.g. smokestack in an incineration plant), the challenge for extractive measurements, where the measurement gas is guided through a gas cell situated between the laser and the detector, is to create a long absorption distance over a small space. This is usually done by using a multi-reflection gas cell, such as a Herriott or White cell, in which the optical path length and therefore the absorption distance is enlarged by means of multiple reflection of the light between mirrors. A weakness of gas cells of this type, however, is their sensitivity with reference to environmental influences such as temperature fluctuations or vibrations. Thus, relatively small changes in geometric parameters, such as the laser's beaming angle or the angles and spacings of the mirrors, can result in major changes in the optical path length and therefore the absorption distance, particularly if the quantity of reflections varies as a result.

SUMMARY OF THE INVENTION

In view of the foregoing, it is therefore an object of the invention to provide a method and absorption spectrometer to compensate for the influence of changes in the optical path length in the absorption spectrometer on the measured result.

This and other objects and advantages are achieved in accordance with the invention by a method and absorption spectrometer comprising a variable-wavelength laser, a detector for generating a measurement signal, a multi-reflection gas cell situated in the light path between the laser and the detector and containing the measurement gas, control means for varying the injection current of the laser, to tune the wavelength of the light to a specific absorption line of the gaseous component of interest, and analyzer for analyzing the measurement signal and establishing a measured result for the concentration to be measured where the wavelength of the light from the laser is tuned to the specific absorption line of the gaseous component of interest, the modulated light is routed through the multi-reflection gas cell containing the measurement gas on to the detector, and a measurement signal generated by the detector is analyzed to establish the measured result for the concentration to be measured, where the wavelength of the light from the laser is tuned to the specific absorption line of the gaseous component of interest, the modulated light is routed through the multi-reflection gas cell containing the measurement gas on the a detector, and a measurement signal generated by the detector is analyzed to establish the measured result for the concentration to be measured.

In accordance with a first embodiment of the invention, the light from the laser is modulated via its injection current with at least one pilot frequency in the MHz range. The measurement signal is analyzed for the pilot frequency in a phase-sensitive manner. Phase information obtained in this operation is compared with phase information obtained during calibration of the absorption spectrometer and the measured result is corrected as a function of the difference between the two items of phase information.

The phase of the signal component contained in the measurement signal with the pilot frequency is dependent on the propagation time of the light from the laser to the detector, and therefore on the optical path distance. With regard to the short path distances between the gas cell and the laser and the detector, the absorption distance is largely identical to the optical path distance due to the multiple reflections in the multi-reflection gas cell. The pilot frequency in the MHz range corresponds to a wavelength in the meter range, so that changes in the optical path length can be securely captured via the phase information.

Due to interference, the optical path length can change not only between successive measurements but also within each measurement period. Since the changes in the optical path length are captured immediately and simultaneously with the measurement of the absorption, however, the captured optical path length changes can be averaged out for the correction of the measured result.

The measured result, i.e., the concentration of the gaseous component of interest, is determined from the absorption detected at the location of the absorption line and the length of the absorption distance. The absorption distance that is free from interference effects and environmental influences is either known, can be measured or is captured implicitly during the calibration of the absorption spectrometer, if different absorption values are measured at different known concentration values and stored in memory together with the associated concentration values.

In the case of modulation of the laser light with phase-sensitive analysis of the measurement signal for more than one pilot frequency, correspondingly more items of phase information are obtained so that the correction of the measured result becomes more accurate or more robust.

In accordance with a second embodiment of the invention, the light from the laser is modulated via its injection current alternately or simultaneously with two pilot frequencies in the MHz range. Each signal component contained in the measurement signal with the pilot frequencies is analyzed in a phase-sensitive manner. A difference between the items of phase information of the two signal components obtained in this operation is compared with a difference between the items of phase information obtained during calibration of the absorption spectrometer. The measured result is corrected as a function of the relationship between the two differences.

The use of two pilot frequencies and the analysis of the difference between the items of phase information obtained provides the advantage that phase errors or offsets arising during signal generation and signal analysis, and affecting both frequencies equally, cancel each other out. Apart from this, there is greater freedom for selecting suitable frequency values, as will be explained further below.

In accordance with a third embodiment of the invention, the light from the laser is likewise modulated with two pilot frequencies in the MHz range, and each signal component contained in the measurement signal with the pilot frequencies is analyzed in a phase-sensitive manner. The length of the light path is now determined from a difference between the items of phase information of the two signal components obtained in this operation and compared with a length obtained during calibration of the absorption spectrometer or the known length of the light path. The measured result is corrected as a function of the relationship between the two lengths.

Here, the advantage consists in the fact that the instantaneous (actual) length of the light path is measured immediately via the difference between the items of phase information obtained, so that a simple correction of the measured result is possible with reference to the known length, or target length as established by calibration, of the light path.

In accordance with a fourth embodiment of the invention, the light from the laser is once again modulated with two pilot frequencies in the MHz range, where each signal component contained in the measurement signal with the pilot frequencies is analyzed in a phase-sensitive manner. The length of the light path is determined from the difference between the items of phase information of the two signal components obtained in this operation, with the aid of which the measured result is determined immediately from the absorption represented by the measurement signal.

Given direct measurement of the reduction in absorption, i.e., in the case of direct absorption spectroscopy, it is invariably possible to determine the correct concentration of the gaseous component of interest immediately from the absorption. The instantaneous length of the light path is measured immediately via the difference between the items of phase information obtained. Consequently, the measurement signal can then immediately become the measured result for the concentration to be measured.

Where the absorption spectrometer in accordance with disclosed embodiments is operated based on wavelength-modulation spectroscopy, the pilot frequency or one of the pilot frequencies can be used advantageously as the modulation frequency, where, in the intrinsically known manner, the measurement signal is demodulated at a higher harmonic, and in particular the second harmonic, of the pilot frequency used as the modulation frequency and analyzed to establish the measured result.

In general, the pilot frequency or pilot frequencies should be selected sufficiently low so that, in the case of the expected or maximum tolerable changes in the optical path length, phase responses greater than $\pi$ are prevented, so that the phase information obtained is unambiguous. In the case of modulation of the light with phase-sensitive analysis of the measurement signal with two pilot frequencies, the advantageous possibility arises to select one pilot frequency sufficiently high so that in the case of a maximum tolerable change in the optical path distance between the laser and the detector, the phase information obtained in this operation changes by more than $k \cdot \pi$ ($k \geq 1$), and the other pilot frequency is selected sufficiently low so that in the case of the maximum tolerable change in the optical path distance, the phase information obtained in this operation changes by less than $\pi$. The value k in the phase information from the higher pilot frequency can then be determined on the basis of the phase information from the lower pilot frequency. In this way, a high angular resolution is achieved by analyzing the measurement signal at the higher pilot frequency, with the associated ambiguous situation being turned into an unambiguous situation again by using the phase information from the lower pilot frequency.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To provide further explanation of the invention, reference is made below to the figures in the drawings, in which.

DETAILED DESCRIPTION OF THE EXEMPLARY EMBODIMENTS

Figure 1:
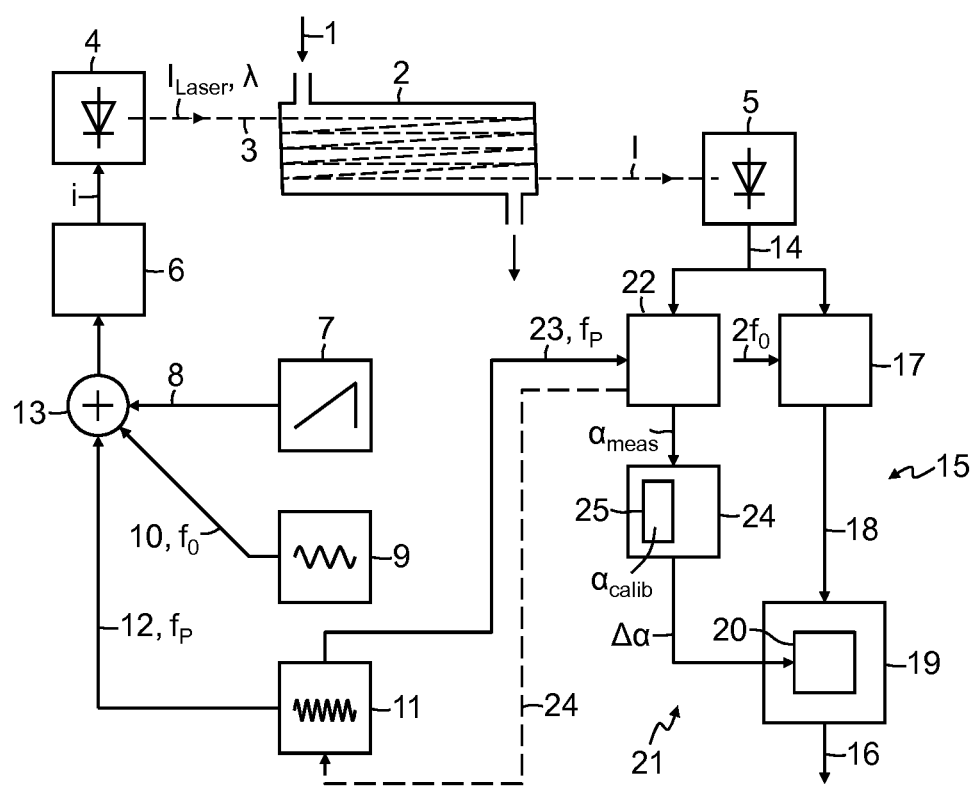
FIG. 1 is a schematic block diagram of an exemplary absorption spectrometer in accordance with the invention.

In the form of a simplified block diagram, FIG. 1 shows an absorption spectrometer operating based on wavelength-modulation spectroscopy (WMS) for measuring the concentration of at least one gaseous component of interest in a measurement gas 1, which is routed through a multi-reflection gas cell 2. The multi-reflection gas cell 2 is arranged in the light path 3 between a laser 4, in this case a laser diode, and a detector 5. The light coming from the laser 4 is reflected multiple times in the multi-reflection gas cell 2 prior to falling on to the detector 5. The multi-reflection gas cell 2 comprises, for example, a Herriott cell or White cell, so that its actual construction can differ considerably from the strongly schematic representation in this case. The laser diode 4 is activated by a controllable current source 6 with an injection current i, with the intensity $I_{Laser}$ and wavelength $\lambda$ of the light generated being dependent on the current i and the operating temperature of the laser diode 4. The current source 6 is activated periodically by a first signal generator 7 with a predefined, preferably sawtooth or triangular, function 8 to scan a selected absorption line of the gaseous component of interest with the wavelength $\lambda$ of the light generated, where the wavelength follows the profile of the current i in a more or less linear manner. A second signal generator 9 generates a sinusoidal modulation signal 10 with a modulation frequency $f_0$ in the kHz range, and a third signal generator (pilot signal generator) 11 a sinusoidal pilot signal 12 with a pilot frequency $f_P$ in the MHz range, with the aid of both of which the sawtooth or triangular function 8 is modulated in a summing element 13.

As a function of the detected light intensity I, the detector 5 generates a detector signal or measurement signal 14, which is analyzed in analyzer 15 to establish a measured result 16 for the concentration of the gaseous component of interest to be measured. Due to the non-linear profile of the scanned absorption line, modulation of the current i for the laser diode 4 with the modulation frequency $f_0$ results in a corresponding variation in the detected light intensity I with more or less marked harmonic distortions. The second harmonic with the frequency $2f_0$ dominates at the location of the absorption maximum and decreases strongly in wavelength ranges away from the center of the absorption line. As a result, it is particularly suitable for further analysis. In principle, any other harmonic can also be used for analysis. In the exemplary embodiment shown, the measurement signal 14 is demodulated in a phase-sensitive manner in a first lock-in amplifier 17, at the second harmonic $2f_0$ of the modulation frequency $f_0$. The demodulated measurement signal 18 becomes the measured result 16 for each scanning interval in an analysis device 19. The analysis is effected in this case, for example, by curve-fitting the ideal profile of the demodulated measurement signal, as described analytically in an approximation model 20, to the profile of the measured demodulated measurement signal 16. The approximation model 20 contains a large number of parameters, also including a parameter for the length of the absorption distance in the multi-reflection gas cell 2 and a parameter for the concentration of the gaseous component to be determined. The result of the analysis and therefore the measured result obtained via the latter parameter is the concentration of the gaseous component to be measured.

A further analyzer 21 is used to analyze the measurement signal 14 for the pilot frequency $f_P$ in a phase-sensitive manner. To this end, the measurement signal 14 is detected in a phase-sensitive manner in a second lock-in amplifier or phase detector 22 at the location of the pilot frequency $f_P$ in the known manner. Here, the measurement signal 14 is demodulated in a phase-sensitive manner, via multiplication by a reference signal 23 supplied by the pilot signal generator 11 having the pilot frequency $f_P$, or directly by the pilot signal 12. The in-phase component I of the demodulated measurement signal is obtained by subsequent low-pass filtering. In the case of a two-phase lock-in amplifier, the measurement signal 14 is additionally multiplied by the reference signal 23 phase-shifted by 90° and via low-pass filtering. The quadrature component Q of the demodulated measurement signal is obtained via subsequent low-pass filtering. The phase $\alpha_{meas}$ of the measurement signal is then given by $\alpha_{meas}$=arctan (Q/I). It is also possible, via feedback coupling, to shift the phase during generation of the reference signal 23 or pilot signal 12 in the pilot signal generator 11 such that the quadrature component becomes zero, with the phase shift of the phase information sought then corresponding to $\alpha_{meas}$.

The phase information obtained $\alpha_{meas}$ is compared in an arithmetic unit 24 with an item of phase information $\alpha_{calib}$ obtained during calibration of the absorption spectrometer and stored in a memory 25. As will be explained in more detail below, the difference $\Delta\alpha$ between the two items of phase information is proportional to an instantaneous change in the length of the absorption distance with respect to the calibration status of the absorption spectrometer. Since, as mentioned above, the approximation model 20 contains a parameter for the length of the absorption distance, the measured result 18 can be corrected immediately in the analysis device 19 as a function of the difference $\Delta\alpha$ between the items of phase information.

The phase of the signal component contained in the measurement signal 14 with the pilot frequency $f_P$ is dependent on the propagation time and/or the optical path distance of the light from the laser 4 to the detector 5. Due to the multiple reflections in the multi-reflection gas cell 2, this path distance corresponds approximately to the absorption distance inside the gas cell 2. The pilot frequency $f_P$ in the MHz range corresponds to a wavelength in the meter range, so that changes in the length of the absorption distance can be captured via the phase information supplied by the second lock-in amplifier 19.

The change $\Delta L$ in the length of the absorption distance is given by:

$$\Delta L = \frac{c}{f_P} \cdot \frac{\Delta\alpha}{2\pi}, \qquad \text{Eq. 1}$$

where c is the speed of light in the measurement gas and $\Delta\alpha$ is the change in the phase of the signal component contained in the measurement signal 18 with the pilot frequency $f_P$.

For example, with a geometric length of the gas cell 2 of 20 cm and predefined 125 reflections, an absorption distance of 25 m is produced. If the light leaves the gas cell 2 at the next earlier or next later time point respectively, i.e., after 123 or 127 reflections, then the absorption distance changes each time by 40 cm. To capture a variation in the absorption distance of ±40 cm via the phase of the signal component contained in the measurement signal 14 with the pilot frequency $f_P$, therefore, its wavelength should be at least 80 cm, i.e., the pilot frequency $f_P$ should be smaller than 375 MHz.

As already mentioned, the absorption is approximately proportional to the product of the concentration value and the length of the absorption distance in the case of small concentrations of the gaseous component to be measured. This means that an absorption A measured during calibration of the absorption spectrometer is given by:

$$A = 1 - e^{-a \cdot c_{calib} \cdot L_0} \approx a \cdot c_{calib} \cdot L_0, \qquad \text{Eq. 2}$$

where a is the absorption coefficient of the gaseous component used during the calibration, $c_{calib}$ is the known concentration of the gaseous component, and $L_0$ is the known absorption distance with no interference effects.

If this same absorption A is measured at a later point during measurement operations as during the calibration, then assuming an unchanged length $L_0$ of the absorption distance, a concentration measured value $c_{meas} = c_{calib}$ is produced. In fact, however, the length of the absorption distance may have changed to $L = L_0 + \Delta L$, so that the correct or corrected concentration measured value $c_{corr}$ is different from the calibration value $c_{calib}$:

$$A = a \cdot c_{corr} \cdot (L_0 + \Delta L). \qquad \text{Eq. 3}$$

The concentration measured value $c_{meas}$ as established can then be corrected as follows by using equation Eq. 1:

$$c_{corr} = c_{meas} \cdot \frac{L_0}{(L_0 + \Delta L)} = c_{meas} \cdot \frac{1}{\left(1 + \frac{1}{L_0} \cdot \frac{c}{f_P} \cdot \frac{\Delta\alpha}{2\pi}\right)}, \qquad \text{Eq. 4}$$

where $c_{corr}$ is the corrected concentration measured value and $\Delta\alpha$ is the difference $\alpha_{meas} - \alpha_{calib}$ between the items of phase information obtained during the current measurement and during the calibration.

Equation 1 applies in the greatly simplified case of a single light propagation path inside the multi-reflection gas cell 2. In fact, however, the propagation path can change not only from one measurement period to another but also within one measurement period. The changes $\Delta L$ in the optical path length are measured immediately and simultaneously with that of the absorption A. As a result, changes in the optical path length occurring within one measurement period are also captured by the correction. Any change in the distribution between the different path lengths present is likewise corrected. Thus, it can be the case, for example, where there is a non-ideal cross-section or diameter of the laser beam, that different components of the laser beam are reflected more or less frequently. This composition of the path lengths and therefore the average path length can change as a result of an interference effect, an element that is detected via the phase change $\Delta\alpha$.

The length $L_0$ of the absorption distance free of interference effects and environmental influences that is needed for correction of the concentration measured value $c_{meas}$ is either known or is captured implicitly during the calibration of the absorption spectrometer, if, in the presence of different known concentration values, different absorption values are measured and stored in memory together with the associated concentration values. As shown in the following, however, the length $L_0$ can also be measured.

Figure 2:
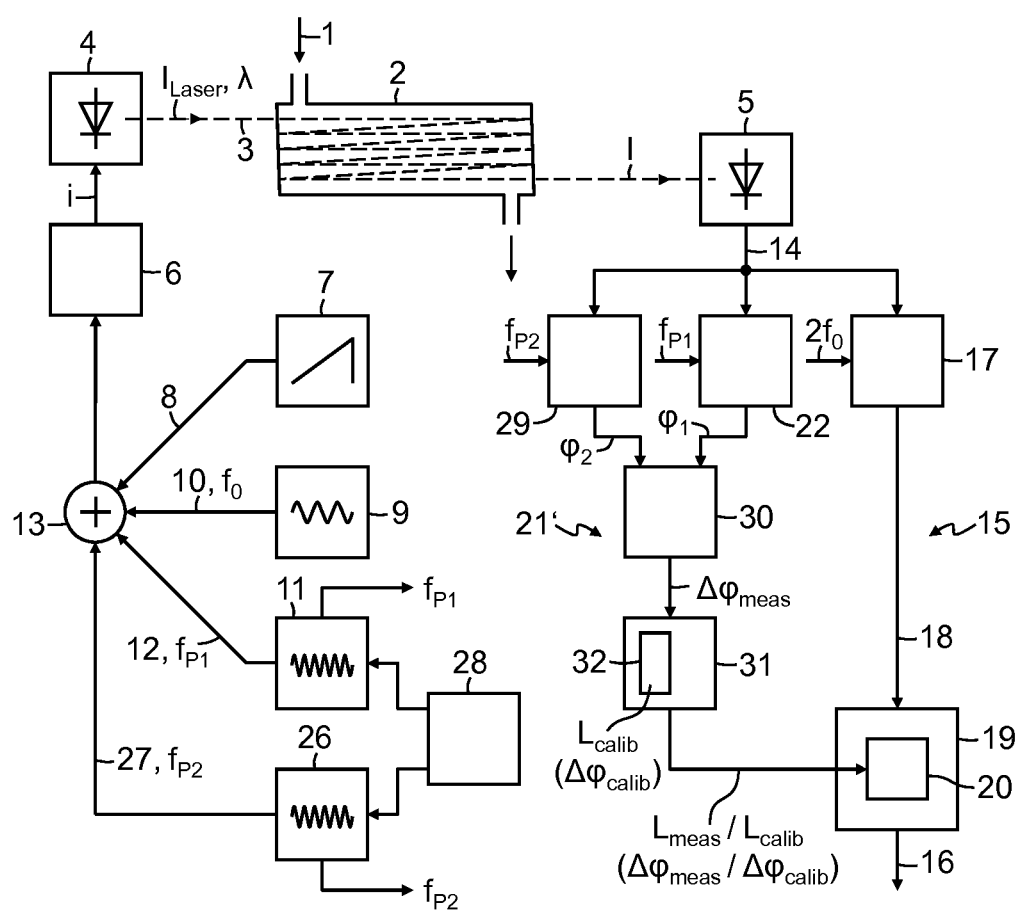
FIG. 2 is a schematic block diagram of an alternative the absorption spectrometer in accordance with the invention.

FIG. 2 shows a second exemplary embodiment of the inventive absorption spectrometer, which, unlike the example depicted in FIG. 1, operates with two pilot frequencies $f_{P1}$ and $f_{P2}$. As in the example of FIG. 1, a laser 4 is activated via a current source 6 with an injection current i, which follows a sawtooth or triangular function 8 generated periodically by a first signal generator 7. Superposed on this function 8 are a sinusoidal modulation signal 10 with a modulation frequency $f_0$ in the kHz range and a first sinusoidal pilot signal 12 with a first pilot frequency $f_{P1}$ in the MHz range, which are generated by a second signal generator 9 and/or a third signal generator (first pilot signal generator) 11. Additionally, a fourth signal generator (second pilot signal generator) 26 generates a second sinusoidal pilot signal 27 with a second pilot frequency $f_{P2}$, which likewise lies in the MHz range but is different from the first pilot frequency $f_{P1}$. The sawtooth or triangular function 8 is additionally modulated with this second pilot signal 27.

In the exemplary embodiment shown, the two pilot signals 12, 27 are generated simultaneously. However, they can also be generated alternately by the two pilot signal generators 11, 26 or by just one pilot signal generator, e.g. 11, by changing the pilot frequency $f_P$ while retaining the phase position. For this purpose, the pilot signal generators 11, 26 can be activated correspondingly by a synchronizing device 28.

After passing through a multi-reflection gas cell 2 containing a measurement gas 1 with a gaseous component of interest, the light coming from the laser 4 falls on to a detector 5, the detector signal or measurement signal 14 from which is analyzed in analyzer 15 to establish a measured result 16 for the concentration of the gaseous component of interest to be measured.

A further analyzer 21' is used to analyze each signal component contained in the measurement signal 14 with the pilot frequencies $f_{P1}$, $f_{P2}$ in a phase-sensitive manner. To this end, the measurement signal 14 is detected in a phase-sensitive manner in a second lock-in amplifier or phase detector 22 at the location of the pilot frequency $f_{P1}$ and in a third lock-in amplifier or phase detector 29 at the location of the pilot frequency $f_{P1}$ in the known manner, where items of phase information $\varphi_1$, $\varphi_2$ are obtained analogously to the example described on the basis of FIG. 1. If, as mentioned above, the pilot frequency $f_P$ is switched over between two values while retaining the phase position, then the two items of phase information are determined via time-division demultiplexing. The difference $\Delta\varphi_{meas}$ between the measured items of phase information $\varphi_1$, $\varphi_2$ is determined in a first arithmetic unit 30. As will be explained in further detail below, the instantaneous optical path length or instantaneous length of the absorption distance $L_{meas}$ can be calculated from this difference $\Delta\varphi_{meas}$ in a second arithmetic unit 31. Since, as already mentioned, the approximation model 20 contains a parameter for the length of the absorption distance, the measured result 18 can be corrected immediately as a function of the currently measured length of the absorption distance $L_{meas}$ in the analysis device 19.

The length L of the absorption distance is given by:

$$L = \left(n + \frac{\ddot{o}_1}{2\pi}\right)\frac{c}{f_{P1}} = \left(m + \frac{\varphi_2}{2\pi}\right)\frac{c}{f_{P2}}, \qquad \text{Eq. 5}$$

where
n is the quantity of full oscillations of the signal component contained in the measurement signal 14 with the first pilot frequency $f_{P1}$ during the propagation time of the light from the laser 4 to the detector 5, and
m is the corresponding quantity of full oscillations of the signal component with the second pilot frequency $f_{P2}$.

It follows from this that the measured phase difference is given by:

$$\Delta\varphi_{meas} = \varphi_1 - \varphi_2 = \left(L_{meas}\frac{2\pi f_{P1}}{c} - n\cdot 2\pi\right) - \qquad \text{Eq. 6}$$
$$\left(L_{meas}\frac{2\pi f_{P2}}{c} - m\cdot 2\pi\right)$$
$$= L_{meas}\frac{2\pi(f_{P1} - f_{P2})}{c} - (n-m)\cdot 2\pi,$$

If n and m are known, the currently measured length of the absorption distance is given by:

$$L_{meas} = \frac{c}{f_{P1} - f_{P2}}\cdot\left(\frac{\Delta\varphi_{meas}}{2\pi} + (n-m)\right), \qquad \text{Eq. 7}$$

or specifically for n=m:

$$L_{meas} = \frac{c}{f_{P1} - f_{P2}}\cdot\frac{\Delta\varphi_{meas}}{2\pi}. \qquad \text{Eq. 8}$$

The measured concentration measured value $c_{meas}$ can then be corrected by using Eq. 8 as follows:

$$c_{corr} = c_{meas}\cdot\frac{L_0}{L_{meas}}. \qquad \text{Eq. 9}$$

The absorption distance free from interference effects and environmental influences $L_0$ is, in itself, known. However, it can also be measured as $L_{calib}$, in the same way as $L_{meas}$, during the calibration of the absorption spectrometer, and stored in a memory 32 of the second arithmetic unit 31. In this case, it is possible to use, in place of the measured absorption distances $L_{meas}$ and $L_{calib}$, the associated differences $\Delta\varphi_{meas}$ and $\Delta\varphi_{calib}$ of the items of phase information $\varphi_1$, $\varphi_2$ measured under measurement and/or calibration conditions. In fact, it follows from equations Eq. 9 and Eq. 8 that:

$$c_{corr} = c_{meas}\cdot\frac{L_{calib}}{L_{meas}} = c_{meas}\cdot\frac{\Delta\varphi_{calib}}{\Delta\varphi_{meas}}. \qquad \text{Eq. 10}$$

In the case of direct measurement of the reduction in absorption, i.e., in the case of direct absorption spectroscopy, it is invariably possible to determine the correct concentration of the gaseous component of interest immediately from the absorption A. In fact, it follows from Eq. 2 and Eq. 8 that:

$$c_{meas} = \frac{A}{a\cdot L_{meas}} = \frac{A}{a}\cdot\frac{f_{P1} - f_{P2}}{c}\cdot\frac{2\pi}{\Delta\varphi}. \qquad \text{Eq. 11}$$

The measured result is not corrected subsequently, therefore, but established directly in correct form. If, on the other hand, the connection between the measured result 16 and the measurement signal 14 cannot be described in an analytical manner immediately, but has to be established via a calibration function, calibration matrix or the like, a subsequent correction of the measured result is normally possible.

The pilot frequencies $f_{P1}$ and $f_{P2}$ should be selected sufficiently low so that in the context of the changes in length $\Delta L$ to be expected for $\varphi_1$ and $\varphi_2$, phase responses greater than $\pi$ are prevented, and therefore n and m remain constant. The same applies to the difference frequency where the difference phase is used. On the other hand, the pilot frequencies $f_{P1}$ and $f_{P2}$ can be selected large enough, by using suitable values for n and m, to achieve an adequate resolution during measurement of the changes in length $\Delta L$.

There is also the option of selecting one of the pilot frequencies, e.g. $f_{P1}$, sufficiently large so that it ensures a high angular resolution, it being possible, however, for the quantity of full oscillations to vary. To restore an unambiguous situation, the other pilot frequency $f_{P2}$ is used, and selected sufficiently low so that the quantity of its full oscillations does not change and the resolution is adequate to determine the quantity of full oscillations for the higher pilot frequency $f_{P1}$. The principle can also be cascaded correspondingly so that small changes in length can also be determined.

In the exemplary disclosed embodiments, essentially only those elements that are necessary for the description of the invention or otherwise helpful are represented. Thus, for example, there has been no detailing of the fact that the injection current i is additionally modulated with a burst signal on a regular basis, e.g., after each scanning period, and that the measurement signal 14 can be automatically amplified and normalized based on the signal components resulting from the burst signal.

The absorption spectrometers shown in the figures can alternatively operate on the basis of direct absorption spectroscopy. In this respect, the second signal generator 9 and the first lock-in amplifier 17 do not apply. The absorption is established directly by virtue of the fact that the profile of the measurement signal 14, which profile essentially corresponds to the shape of the absorption line, is analyzed immediately.

Figure 3:
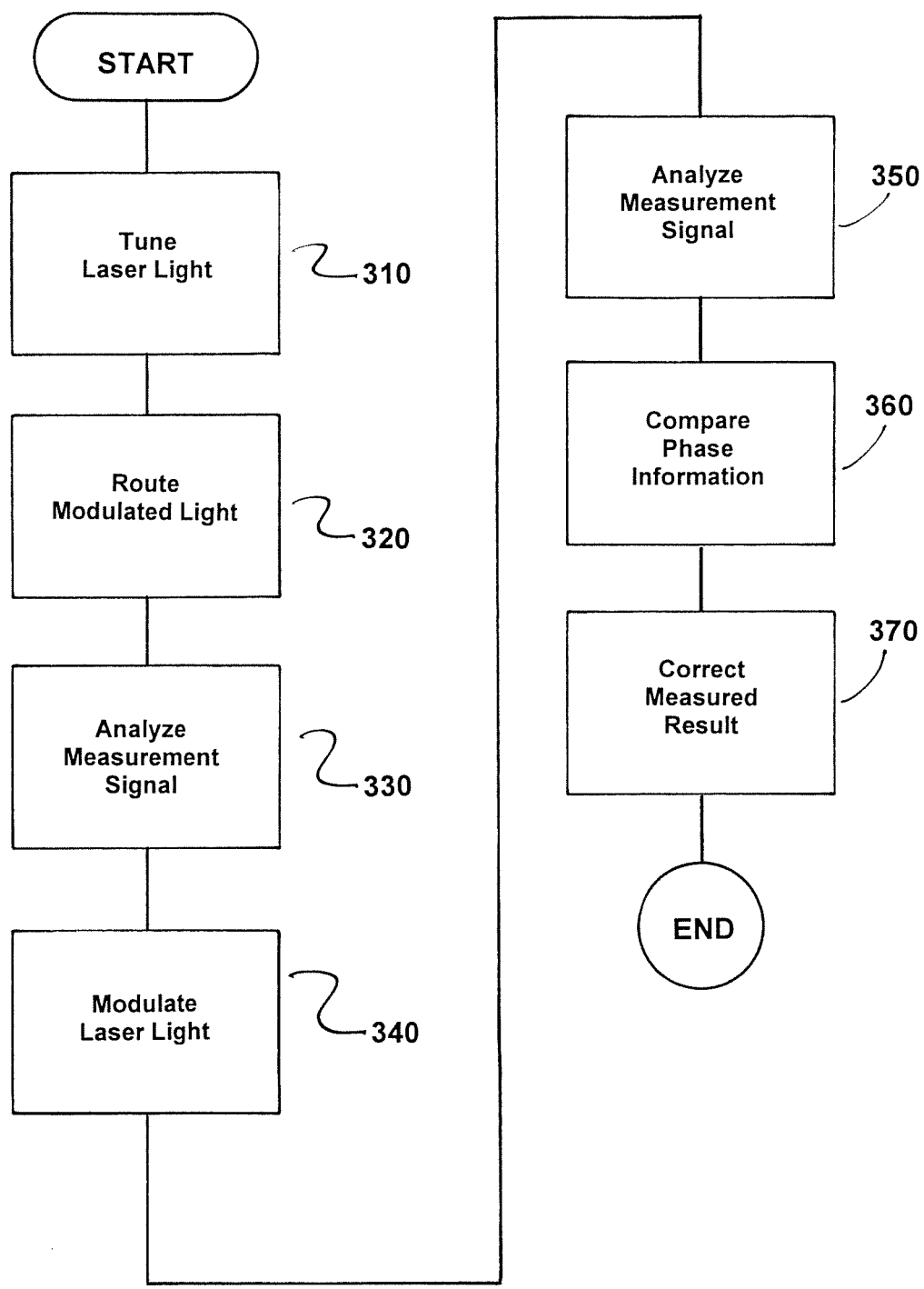
FIG. 3 is a flowchart of the method in accordance with an embodiment of the invention.

FIG. 3 is a flowchart of a method for measuring a concentration of a gaseous component of interest in a measurement gas (1). The method comprises tuning a wavelength of light from a laser (4) to a specific absorption line of the gaseous component of interest, as indicated in step 310. Next, a modulated light is routed through a multi-reflection gas cell (2) containing the measurement gas (1) on to a detector (5), as indicated in step 320.

A measurement signal (14) generated by the detector (5) is then analyzed to establish a measured result (16) for a concentration to be measured, as indicated in step 330.

The light from the laser (4) is now modulated with at least one pilot frequency ($f_P$) in a MHz range, as indicated in step 340. Next, the measurement signal (14) for a pilot frequency ($f_P$) is analyzed in a phase-sensitive manner, as indicated in step 350. Next, phase information ($\alpha_{meas}$) obtained during the analyzing is compared with phase information ($\alpha_{calib}$) obtained during calibration of the absorption spectrometer, as indicated in step 360.

The measured result (16) is now corrected as a function of a difference ($\Delta\alpha$) between two items of phase information ($\alpha_{meas}$, $\alpha_{calib}$) as indicated in step 370.

Figure 4:
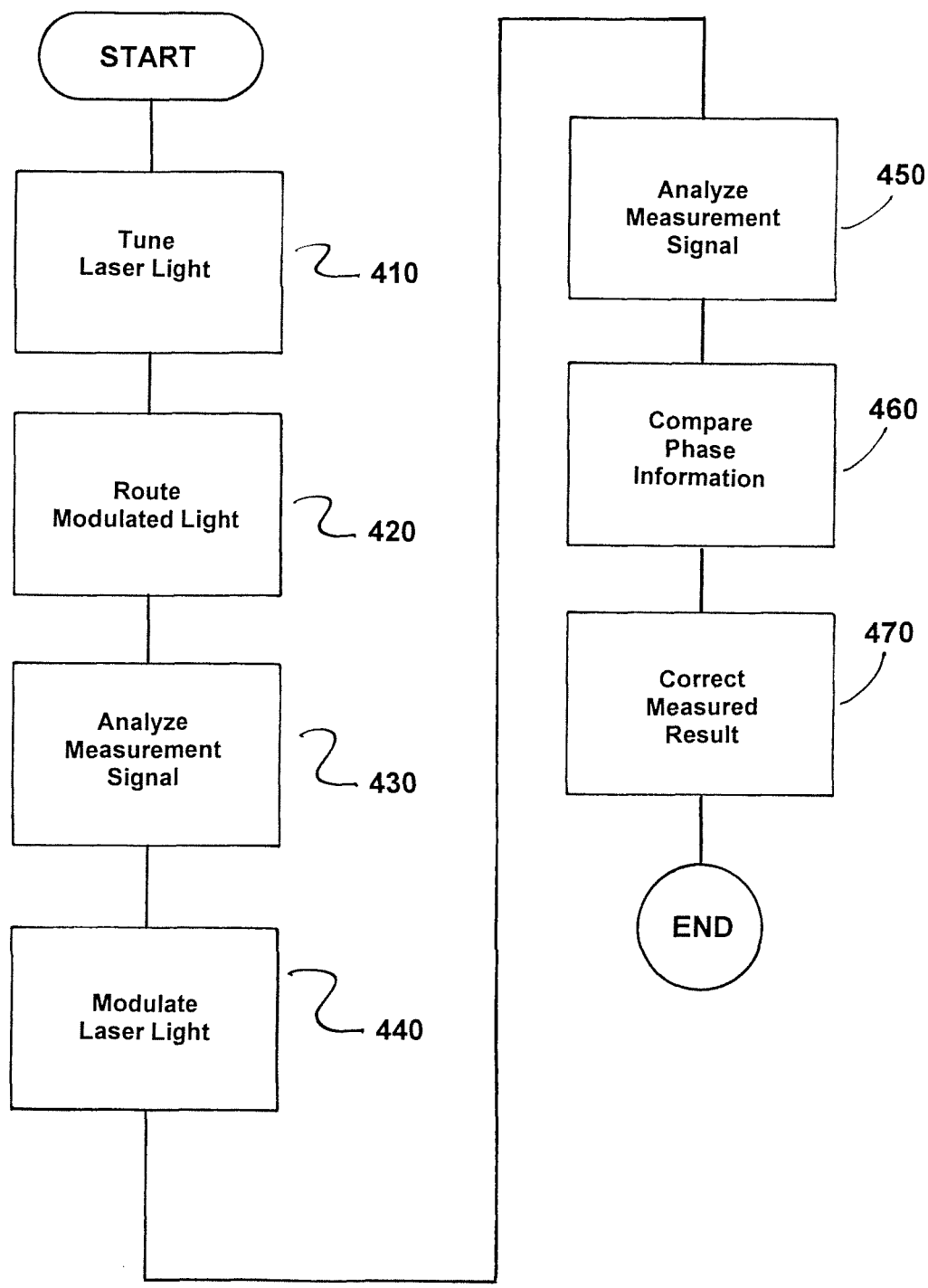
FIG. 4 is a flowchart of the method in accordance with an alternative embodiment of the invention.

FIG. 4 a flowchart of a method for measuring the concentration of a gaseous component of interest in a measurement gas (1) in accordance with an alternative embodiment. The method comprises tuning a wavelength of light from a laser (4) to a specific absorption line of the gaseous component of interest, as indicated in step 410.

Next, modulated light is routed through a multi-reflection gas cell (2) containing the measurement gas (1) onto a detector (5), as indicated in step 420.

A measurement signal (14) generated by the detector (5) is analyzed to establish a measured result (16) for a concentration to be measured, as indicated in step 430.

Next, the light from the laser (4) is modulated alternately or simultaneously with a plurality of pilot frequencies ($f_{P1}$, $f_{P2}$) in a MHz range, as indicated in step 440.

Each signal component contained in the measurement signal (14) with the plurality of pilot frequencies ($f_{P1}$, $f_{P2}$) is analyzed in a phase-sensitive manner, as indicated in step 450.

Next, the difference ($\Delta\varphi_{meas}$) between items of phase information ($\varphi_1$, $\varphi_2$) of two signal components obtained during the analysis is compared with the difference ($\Delta\varphi_{calib}$) between items of phase information obtained during calibration of the absorption spectrometer, as indicated in step 460.

The measured result (16) is now corrected as a function of the relationship between the two differences ($\Delta\varphi_{meas}$, $\Delta\varphi_{calib}$) as indicated in step 470.

Figure 5:
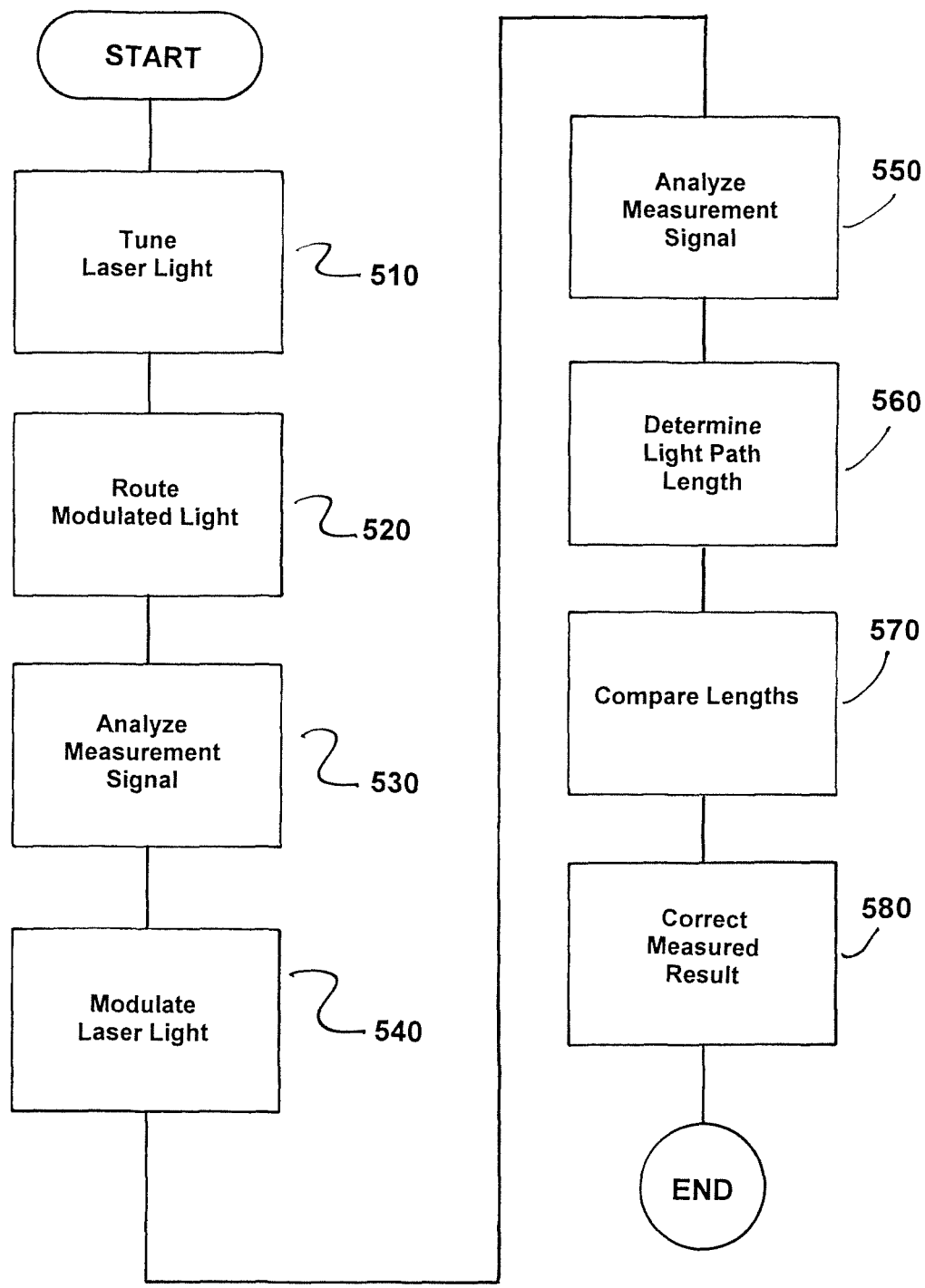
FIG. 5 is a flowchart of the method in accordance with a further embodiment of the invention.

FIG. 5 is a flowchart of a method for measuring a concentration of a gaseous component of interest in a measurement gas (1) in accordance with another embodiment. The method, comprises tuning a wavelength of light from a laser (4) to a specific absorption line of the gaseous component of interest, as indicated in step 510.

Next, modulated light is routed through a multi-reflection gas cell (2) containing the measurement gas (1) onto a detector (5), as indicated in step 520.

Next, a measurement signal (14) generated by the detector (5) is analyzed to establish a measured result (16) for a concentration to be measured, as indicate in step 530.

The light from the laser (4) is now modulated alternately or simultaneously with a plurality of pilot frequencies ($f_{P1}$, $f_{P2}$) in a MHz range, as indicated in step 540.

Next, each signal component contained in the measurement signal (14) with the plural of pilot frequencies ($f_{P1}$, $f_{P2}$) is analyzed in a phase-sensitive manner, as indicted in step 550.

A length ($L_{meas}$) of the light path (3) is now determined from a difference ($\Delta\varphi_{meas}$) between items of phase information ($\varphi_1$, $\varphi_2$) of the plurality of signal components obtained during the analysis, as indicated in step 560.

Next, the determined length is compared with a length ($L_{calib}$) obtained during calibration of the absorption spectrometer or a known length ($L_0$) of the light path (3), as indicated in step 570.

The measured result (16) is now corrected as a function of the relationship between the two lengths ($L_{meas}$, $L_{calib}$ or $L_0$), as indicated in step 580.

Figure 6:
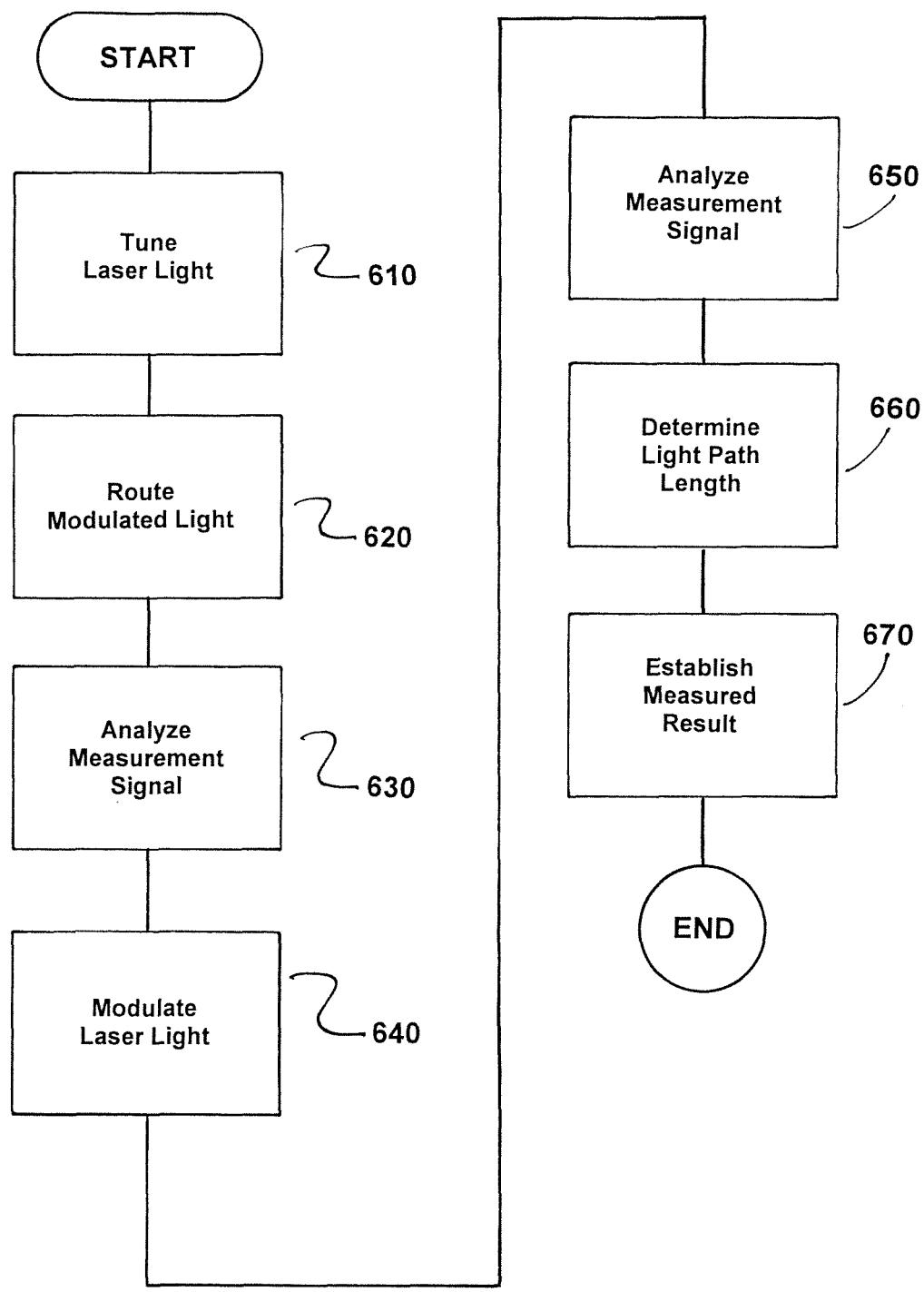
FIG. 6 is a flowchart of the method in accordance with another embodiment of the invention.

FIG. 6 is a flowchart of the method for measuring a concentration of a gaseous component of interest in a measurement gas (1) in accordance with a further embodiment. The method comprises tuning a wavelength of light from a laser (4) to a specific absorption line of the gaseous component of interest, as indicated in step 610.

Next, modulated light is routed through a multi-reflection gas cell (2) containing the measurement gas (1) onto a detector (5), as indicated in step 620.

Next, a measurement signal (14) generated by the detector (5) is analyzed to establish a measured result (16) for a concentration to be measured, as indicated in step 630.

The light from the laser (4) is now modulated alternately or simultaneously with a plurality of pilot frequencies ($f_{P1}$, $f_{P2}$) in a MHz range, as indicated in step 640.

Next, each signal component contained in the measurement signal (14) with the plurality of pilot frequencies ($f_{P1}$, $f_{P2}$) is analyzed in a phase-sensitive manner, as indicated in step 650.

A length ($L_{meas}$) of the light path (3) is then determined from a difference ($\Delta\varphi_{meas}$) between items of phase information ($\varphi_1$, $\varphi_2$) of the plurality of signal components obtained during the analysis, as indicated in step 660.

The measured result (16) is now established immediately with the determined length from an absorption represented by the measurement signal (14), as indicated in step 670.

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An absorption spectrometer for measuring the concentration of a gaseous component of interest in a measurement gas, comprising:
   a variable-wavelength laser;
   a detector for generating a measurement signal;
   a multi-reflection gas cell arranged in a light path between the variable-wavelength laser and the detector and containing the measurement gas;
   a controller configured to vary an injection current (i) of the variable-wavelength laser and to tune a wavelength of light to a specific absorption line of the gaseous component of interest, the controller including at least one pilot signal generator configured to modulate the injection current (i) alternately or simultaneously with at least two pilot frequencies ($f_{P1}$, $f_{P2}$) in a MHz range;
   an analyzer configured to analyze the measurement signal and establish a measured result for the concentration to be measured; and a further analyzer configured to analyze each signal component of at least two signal components contained in the measurement signal with the at least two pilot frequencies ($f_{P1}$, $f_{P2}$) in a phase-sensitive manner, to compare a difference ($\Delta\varphi_{meas}$) between items of phase information ($\varphi_1$, $\varphi_2$) of the at least two signal components obtained in this operation with a difference ($\Delta\varphi_{calib}$) between items of phase information obtained during calibration of the absorption spectrometer, and configured to correct the measured result as a function of a relationship between the two differences ($\Delta\varphi_{meas}$, $\Delta\varphi_{calib}$).

2. The absorption spectrometer as claimed in claim 1, wherein said absorption spectrometer functions based on wavelength-modulation spectroscopy with at least one pilot frequency of the at least two pilot frequencies ($f_{P1}$, $f_{P2}$) as a modulation frequency, wherein the analyzer is formed so as to analyze the measurement signal at a higher harmonic ($nf_{P1}$, $nf_{P2}$) of the at least one pilot frequency ($f_{P1}$, $f_{P2}$) used as the modulation frequency to establish the measured result.

3. The absorption spectrometer as claimed in claim 2, wherein the higher harmonic is a second harmonic ($2f_{P1}$, $2f_{P2}$).

4. An absorption spectrometer for measuring the concentration of a gaseous component of interest in a measurement gas, comprising:
   a variable-wavelength laser;
   a detector for generating a measurement signal;
   a multi-reflection gas cell arranged in a light path between the variable-wavelength laser and the detector and containing the measurement gas;
   a controller configured to vary an injection current (i) of the variable-wavelength laser and to tune the wavelength of light to a specific absorption line of the gaseous component of interest, the controller including at least one pilot signal generator to modulate the injection current (i) alternately or simultaneously with at least two pilot frequencies ($f_{P1}$, $f_{P2}$) in a MHz range;
   an analyzer configured to analyze the measurement signal and establish a measured result for a concentration to be measured; and
   a further analyzer configured to analyze each signal component of at least two signal components contained in the measurement signal with the at least two pilot frequencies ($f_{P1}$, $f_{P2}$) in a phase-sensitive manner, to determine a length ($L_{meas}$) of the light path from a difference ($\Delta\varphi_{meas}$) between items of phase information ($\varphi_1$, $\varphi_2$) of the at least two signal components obtained in this operation, to compare said determined length with a length ($L_{calib}$) obtained during calibration of the absorption spectrometer or a known length ($L_0$) of the light path, and to correct the measured result as a function of a relationship between the two lengths ($L_{meas}$, $L_{calib}$ or $L_0$).

5. The absorption spectrometer as claimed in claim 4, wherein said absorption spectrometer functions based on wavelength-modulation spectroscopy with at least one pilot frequency of the at least two pilot frequencies ($f_{P1}$, $f_{P2}$) as a modulation frequency, wherein the analyzer is formed so as to analyze the measurement signal at a higher harmonic ($nf_{P1}$, $nf_{P2}$) of the at least one pilot frequency ($f_{P1}$, $f_{P2}$) used as the modulation frequency to establish the measured result.

6. The absorption spectrometer as claimed in claim 5, wherein the higher harmonic is a second harmonic ($2f_{P1}$, $2f_{P2}$).

7. An absorption spectrometer for measuring the concentration of a gaseous component of interest in a measurement gas, comprising:
   a variable-wavelength laser;
   a detector for generating a measurement signal;
   a multi-reflection gas cell arranged in a light path between the laser and the detector and containing the measurement gas;
   a controller configured to vary an injection current (i) of the variable-wavelength laser and to tune a wavelength of the light to a specific absorption line of the gaseous component of interest, the controller including at least one pilot signal generator to modulate the injection current (i) alternately or simultaneously with at least two pilot frequencies ($f_{P1}$, $f_{P2}$) in a MHz range;
   an analyzer configured to analyze the measurement signal and establish a measured result for a concentration to be measured; and
   a further analyzer configured to analyze each signal component of at least two signal components contained in the measurement signal with the at least two pilot frequencies ($f_{P1}$, $f_{P2}$) in a phase-sensitive manner and to determine a length ($L_{meas}$) of the light path from a difference ($\Delta\varphi_{meas}$) between items of phase information ($\varphi_1$, $\varphi_2$) of the at least two signal components obtained in this operation, with the aid of which the measured result is immediately determined from an absorption represented by the measurement signal.

8. The absorption spectrometer as claimed in claim 7, wherein said absorption spectrometer functions based on wavelength-modulation spectroscopy with at least one pilot frequency of the at least two pilot frequencies ($f_{P1}$, $f_{P2}$) as a modulation frequency, wherein the analyzer is formed so as to analyze the measurement signal at a higher harmonic ($nf_{P1}$, $nf_{P2}$) of the at least one pilot frequency ($f_{P1}$, $f_{P2}$) used as the modulation frequency to establish the measured result.

9. The absorption spectrometer as claimed in claim 8, wherein the higher harmonic is a second harmonic ($2f_{P1}$, $2f_{P2}$).

10. A method for measuring the concentration of a gaseous component of interest in a measurement gas, comprising:
    tuning a wavelength of light from a laser to a specific absorption line of the gaseous component of interest;
    routing modulated light through a multi-reflection gas cell containing the measurement gas onto a detector;
    analyzing a measurement signal generated by the detector to establish a measured result for a concentration to be measured;
    modulating the light from the laser alternately or simultaneously with at least two pilot frequencies ($f_{P1}$, $f_{P2}$) in a MHz range;
    analyzing each signal component of at least two signal components contained in the measurement signal with the at least two pilot frequencies ($f_{P1}$, $f_{P2}$) in a phase-sensitive manner;
    comparing a difference ($\Delta\varphi_{meas}$) between items of phase information ($\varphi_1, \varphi_2$) of the at least two signal components obtained during said analyzing with a difference ($\Delta\varphi_{calib}$) between items of phase information obtained during calibration of the absorption spectrometer; and
    correcting the measured result as a function of the relationship between the two differences ($\Delta\varphi_{meas}$, $\Delta\varphi_{calib}$).

11. The method as claimed in claim 10, wherein, in a case of modulation of the light with phase-sensitive analysis of the measurement signal with a plurality of pilot frequencies, one pilot frequency is selected at a level high enough such that in the case of a maximum tolerable change in an optical path distance between the laser and the detector, obtained phase information changes by more than k·π (k≥1), and another pilot frequency is selected at a level low enough such that in the case of the maximum tolerable change in the optical path distance, the obtained phase information changes by less than π, and such that a value k in the phase information from a higher pilot frequency is determined based on phase information from a lower pilot frequency.

12. A method for measuring a concentration of a gaseous component of interest in a measurement gas, comprising:
   tuning a wavelength of light from a laser to a specific absorption line of the gaseous component of interest;
   routing modulated light through a multi-reflection gas cell containing the measurement gas onto a detector;
   analyzing a measurement signal generated by the detector to establish a measured result for a concentration to be measured;
   modulating the light from the laser alternately or simultaneously with at least two pilot frequencies ($f_{P1}$, $f_{P2}$) in a MHz range;
   analyzing each signal component of at least two signal components contained in the measurement signal with the at least two pilot frequencies ($f_{P1}$, $f_{P2}$) in a phase-sensitive manner;
   determining a length ($L_{meas}$) of the light path from a difference ($\Delta\varphi_{meas}$) between items of phase information ($\varphi_1$, $\varphi_2$) of the at least two signal components obtained during said analyzing;
   comparing said determined length with a length ($L_{calib}$) obtained during calibration of the absorption spectrometer or a known length ($L_0$) of the light path; and
   correcting the measured result as a function of a relationship between the two lengths ($L_{meas}$, $L_{calib}$ or $L_0$).

13. The method as claimed in claim 12, wherein, in a case of modulation of the light with phase-sensitive analysis of the measurement signal with a plurality of pilot frequencies, one pilot frequency is selected at a level high enough such that in the case of a maximum tolerable change in an optical path distance between the laser and the detector, obtained phase information changes by more than k·π (k≥1), and another pilot frequency is selected at a level low enough such that in the case of the maximum tolerable change in the optical path distance, the obtained phase information changes by less than π, and such that a value k in the phase information from a higher pilot frequency is determined based on phase information from a lower pilot frequency.

14. A method for measuring a concentration of a gaseous component of interest in a measurement gas, comprising:
   tuning a wavelength of light from a laser to a specific absorption line of the gaseous component of interest;
   routing modulated light through a multi-reflection gas cell containing the measurement gas onto a detector;
   analyzing a measurement signal generated by the detector to establish a measured result for a concentration to be measured;
   modulating the light from the laser alternately or simultaneously with at least two pilot frequencies ($f_{P1}$, $f_{P2}$) in a MHz range;
   analyzing each signal component of at least two signal components contained in the measurement signal with the at least two pilot frequencies ($f_{P1}$, $f_{P2}$) in a phase-sensitive manner;
   determining a length ($L_{meas}$) of the light path from a difference ($\Delta\varphi_{meas}$) between items of phase information ($\varphi_1$, $\varphi_2$) of the at least two signal components obtained during said analyzing; and
   establishing the measured result immediately with the determined length from an absorption represented by the measurement signal.

15. The method as claimed in claim 14, wherein, in a case of modulation of the light with phase-sensitive analysis of the measurement signal with a plurality of pilot frequencies, one pilot frequency is selected at a level high enough such that in the case of a maximum tolerable change in an optical path distance between the laser and the detector, obtained phase information changes by more than k·π (k≥1), and another pilot frequency is selected at a level low enough such that in the case of the maximum tolerable change in the optical path distance, the obtained phase information changes by less than π, and such that a value k in the phase information from a higher pilot frequency is determined based on phase information from a lower pilot frequency.

16. A method for measuring a concentration of a gaseous component of interest in a measurement gas, comprising:
   tuning a wavelength of light from a laser to a specific absorption line of the gaseous component of interest;
   routing a modulated light through a multi-reflection gas cell containing the measurement gas on to a detector;
   analyzing a measurement signal generated by the detector to establish a measured result for a concentration to be measured;
   modulating the light from the laser with at least one pilot frequency ($f_P$) in a MHz range;
   analyzing the measurement signal for a pilot frequency ($f_P$) in a phase-sensitive manner;
   comparing phase information ($\alpha_{meas}$) obtained during said analyzing with phase information ($\alpha_{calib}$) obtained during calibration of the absorption spectrometer; and
   correcting the measured result as a function of a difference ($\Delta\alpha$) between the two items of phase information ($\alpha_{meas}$, $\alpha_{calib}$);
   wherein, in a case of modulation of the light with phase-sensitive analysis of the measurement signal with a plurality of pilot frequencies, one pilot frequency is selected at a level high enough such that in the case of a maximum tolerable change in an optical path distance between the laser and the detector, obtained phase information changes by more than k·π (k≥1), and another pilot frequency is selected at a level low enough such that in the case of the maximum tolerable change in the optical path distance, the obtained phase information changes by less than π, and such that a value k in the phase information from a higher pilot frequency is determined based on phase information from a lower pilot frequency.

* * * * *